United States Patent
Govindjee et al.

(10) Patent No.: US 10,674,952 B1
(45) Date of Patent: *Jun. 9, 2020

(54) DETECTION AND MANAGEMENT OF MEMORY IMPAIRMENT

(71) Applicant: International Business Machines Corporation, Armonk, NY (US)

(72) Inventors: Anita Govindjee, Ithaca, NY (US); Cheng Xu, Beijing (CN); Su Liu, Austin, TX (US); Bing Fang, Ningbo (CN)

(73) Assignee: International Business Machines Corporation, Armonk, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/509,777

(22) Filed: Jul. 12, 2019

Related U.S. Application Data (63) Continuation of application No. 16/196,101, filed on Nov. 20, 2018.

(51) Int. Cl.
*A61B 5/00* (2006.01)
*G16H 50/20* (2018.01)
*G06N 20/00* (2019.01)

(52) U.S. Cl.
CPC ........... *A61B 5/4088* (2013.01); *G06N 20/00* (2019.01); *G16H 50/20* (2018.01)

(58) Field of Classification Search
CPC ....... A61B 5/4088; G16H 50/20; G06N 20/00
USPC ...................................... 340/573.1
See application file for complete search history.

(56) References Cited

U.S. PATENT DOCUMENTS

| | | | |
|---|---|---|---|
| 6,475,161 B2 | 11/2002 | Teicher et al. | |
| 6,549,915 B2* | 4/2003 | Abbott, III | G06F 16/40 |
| 9,177,257 B2 | 11/2015 | Kozloski et al. | |
| 9,514,281 B2 | 12/2016 | Hirst et al. | |
| 2005/0228785 A1 | 10/2005 | Wolcott et al. | |
| 2009/0157672 A1* | 6/2009 | Vemuri | G09B 19/00 |
| 2011/0183309 A1* | 7/2011 | Ochoa | G09B 5/02 |
| | | | 434/365 |
| 2011/0236864 A1 | 9/2011 | Ashford | |

(Continued)

OTHER PUBLICATIONS

Anonymous, "System and Method for Cognitive Shaping via Visual Analysis," An IP.com Prior Art Database Technical Disclosure, IP.com No. IPCOM000244312D, Dec. 1, 2015, 3 pages.

(Continued)

*Primary Examiner* — Kerri L McNally
(74) *Attorney, Agent, or Firm* — Kerlsey M. Skodje (57) ABSTRACT

A system and method for providing reminding assistance. The system includes at least one processing component, at least one memory component, and a memory impairment detection and assistance environment. The memory impairment detection and assistance environment includes a reminding database, an analysis module, and an assistance module. The analysis module includes an attribute analyzer configured to determine values for attributes based on memory impairment detection data and a memory evaluator configured to determine that an attribute has a value that crosses a threshold attribute value. The assistance module includes a reminding assistant configured to receive a memory impairment signal and, in response, generate a reminder that includes information selected from the reminding database.

8 Claims, 5 Drawing Sheets

(56) References Cited

U.S. PATENT DOCUMENTS

| | | | |
|---|---|---|---|
| 2014/0067730 A1* | 3/2014 | Kozloski | G06F 19/3481 |
| | | | 706/12 |
| 2015/0018630 A1 | 1/2015 | Fotuhi | |
| 2015/0072324 A1 | 3/2015 | Pracar et al. | |
| 2016/0125748 A1 | 5/2016 | Ashford | |
| 2016/0317521 A1 | 11/2016 | Chen et al. | |

OTHER PUBLICATIONS

Anonymous, "Context-sensitive personal speech completion aid," An IP.com Prior Art Database Technical Disclosure, IP.com No. IPCOM000236313D, Apr. 18, 2014, 5 pages.

Chinaei et al., "Identifying and Avoiding Confusion in Dialogue with People with Alzheimer's Disease," Computational Linguistics, vol. 43, No. 2, Accepted for Publication: Nov. 7, 2016, pp. 377-406, 2017 Association for Computational Linguistics. DOI: 10.1162/COLI a 00290.

Lee et al., "Lifelogging Memory Appliance for People with Episodic Memory Impairment," UbiComp'08, Proceedings of the 10th International Conference on Ubiquitous Computing, Sep. 2008, pp. 44-53, ACM.

"Preventing Alzheimer's Disease: What Do We Know?" National Institute of Aging, U.S. Department of Health & Human Services, Sep. 24, 2018, pp. 1-6.

Mell et al., "The NIST Definition of Cloud Computing: Recommendations of the National Institute of Standards and Technology," Special Publication 800-145, Sep. 2011, 7 pages, National Institute of Standards and Technology, Gaithersburg, MD.

Scutti, S., "IBM Watson, Using Speech Analysis Techniques, Correctly Identifies Patients At-Risk for Psychosis," Medical Daily, Aug. 26, 2015, 12 pages. https://www.medicaldaily.com/ibm-watson-using-speech-analysis-techniques-correctly-identifies-patients-risk-349794.

Govindjee et al., "Detection and Management of Memory Impairment," U.S. Appl. No. 16/196,101, filed Nov. 20, 2018.

List of IBM Patents or Patent Applications Treated as Related, Signed Jul. 12, 2019, 2 pages.

* cited by examiner

DETECTION AND MANAGEMENT OF MEMORY IMPAIRMENT

BACKGROUND

The present disclosure relates to machine learning and, more specifically, to detecting memory impairment and providing reminders based on the progression of memory loss symptoms.

Impairment of human memory is associated with aging, as well as mild cognitive impairment, certain neurodevelopmental disorders, disorders that cause progressive memory loss (e.g., Alzheimer's disease, vascular dementia, frontotemporal dementia, and Lewy body dementia), and various causes of reversible memory loss (e.g., certain medications or combinations of medications, hypothyroidism, and brain diseases such as tumors or infections). There are currently no treatments that can substantially delay or halt progressive memory loss. Instead, modifications to an affected individual's living environment are typically implemented to manage early to moderate symptoms.

SUMMARY

Various embodiments are directed to a system for providing reminding assistance. The system can include at least one processing component, at least one memory component, and a memory impairment detection (MID) and assistance environment. The memory impairment detection and assistance environment can include a reminding database, a data structure, a collection module, an assistance module, and an analysis module. The analysis module can include an attribute analyzer configured to determine, based on MID data, values for one or more attributes, as well as a memory evaluator configured to determine that at least one attribute from the one or more attributes has a value that crosses a threshold attribute value. The memory evaluator can also be configured to determine, based on the values of the one or more attributes, a level of memory impairment for a designated user. The assistance module can include an information locator and a reminding assistant configured to receive a memory impairment signal and generate a reminder that includes information selected from the reminding database. In some embodiments, the MID data includes the memory impairment signal. The collection module can include a conversation tracker configured to collect conversation data, a content extractor configured to extract the MID data from the conversation data in real time, and a data collector configured to update the data structure with the MID data. The data collector can also be configured to select MID data related to the at least one attribute and update the reminding database with the selected MID data.

Further embodiments are directed to a method for providing reminding assistance. The method can include determining values for one or more attributes based on memory impairment detection (MID) data, as well as determining that at least one attribute from the one or more attributes has a value that crosses a threshold attribute value. Examples of attributes can include frequency of object misplacement, number of missed appointments, difficulty in recognizing family and friends, difficulty in following directions, difficulty in completing a sentence or remaining on topic, confusion about time or location, confusion about people, difficulty in remembering names of common objects or well-known places, difficulty in remembering names of close associates, word specificity, richness of vocabulary, syntactic complexity, word or phrase repetition, number of incomplete words, and number of filler words. The method can also include receiving a memory impairment signal and generating a reminder that includes information selected from a reminding database. The reminder can be displayed on a user interface. Additionally, the method can include determining a level of memory impairment for a designated user based on the values of the one or more attributes. Further, the method can include recording conversation data, extracting MID data from the conversation data in real time, and updating a data structure with the MID data. In some embodiments, the extracted MID data includes the memory impairment signal. The method can also include selecting MID data related to the at least one attribute and updating the reminding database with the selected MID data.

Additional embodiments are directed to a computer program product for providing reminding assistance, the computer program product comprising a computer readable storage medium having program instructions embodied therewith, the program instructions executable by a processor to cause a device to perform a method. The method can include determining values for one or more attributes based on memory impairment detection (MID) data, as well as determining that at least one attribute from the one or more attributes has a value that crosses a threshold attribute value. The method can also include receiving a memory impairment signal and generating a reminder that includes information selected from a reminding database. Additionally, the method can include determining a level of memory impairment for a designated user based on the values of the one or more attributes. Further, the method can include recording conversation data, extracting MID data from the conversation data in real time, and updating a data structure with the MID data. In some embodiments, the extracted MID data includes the memory impairment signal. The method can also include selecting MID data related to the at least one attribute and updating the reminding database with the selected MID data.

DETAILED DESCRIPTION

Detection of memory impairment is used in the diagnosis of various disorders, such as mild cognitive impairment, disorders that cause progressive memory loss (e.g., Alzheimer's disease, vascular dementia, frontotemporal dementia, and Lewy body dementia), hypothyroidism, and brain diseases such as tumors or infections. There are currently no treatments that can halt progressive memory loss associated with dementia, which is most commonly caused by Alzheimer's disease. Instead, modifications to an affected individual's living environment can be implemented to manage early to moderate symptoms. Diagnosing this progressive memory impairment as early as possible can greatly improve the quality of life for an affected individual because it provides time to make arrangements for managing the symptoms and to seek methods of slowing the progression of the impairment.

However, diagnosing dementia is difficult because it can only be detected by observing symptoms of cognitive impairment, which include memory impairment, and then ruling out causes of reversible memory loss. Symptoms of memory impairment are often missed because they develop slowly and can be mistaken for normal forgetfulness. Additionally, affected individuals and those around them frequently adapt compensation strategies that mask the symptoms during the gradual early stages, often without realizing it. Therefore, the dementia is not diagnosed until it is causing severe problems.

Disclosed herein are a system, method, and computer program product for detecting memory impairment, as well as for providing integrated memory analysis and assistance. Memory impairment detection (MID) data is obtained from real-time conversation tracking, as well as other data sources, and used to detect, monitor, and analyze memory impairment. This allows memory deterioration to be detected earlier than what is possible for human observers. Additionally, a cognitive reminding assistant is provided for memory augmentation. The reminding assistant can provide customized assistance to a user based on at least one memory evaluation. For example, the reminding assistant can efficiently obtain information from a reminding database that contains data selected based on the particular symptoms of the user.

Figure 1:
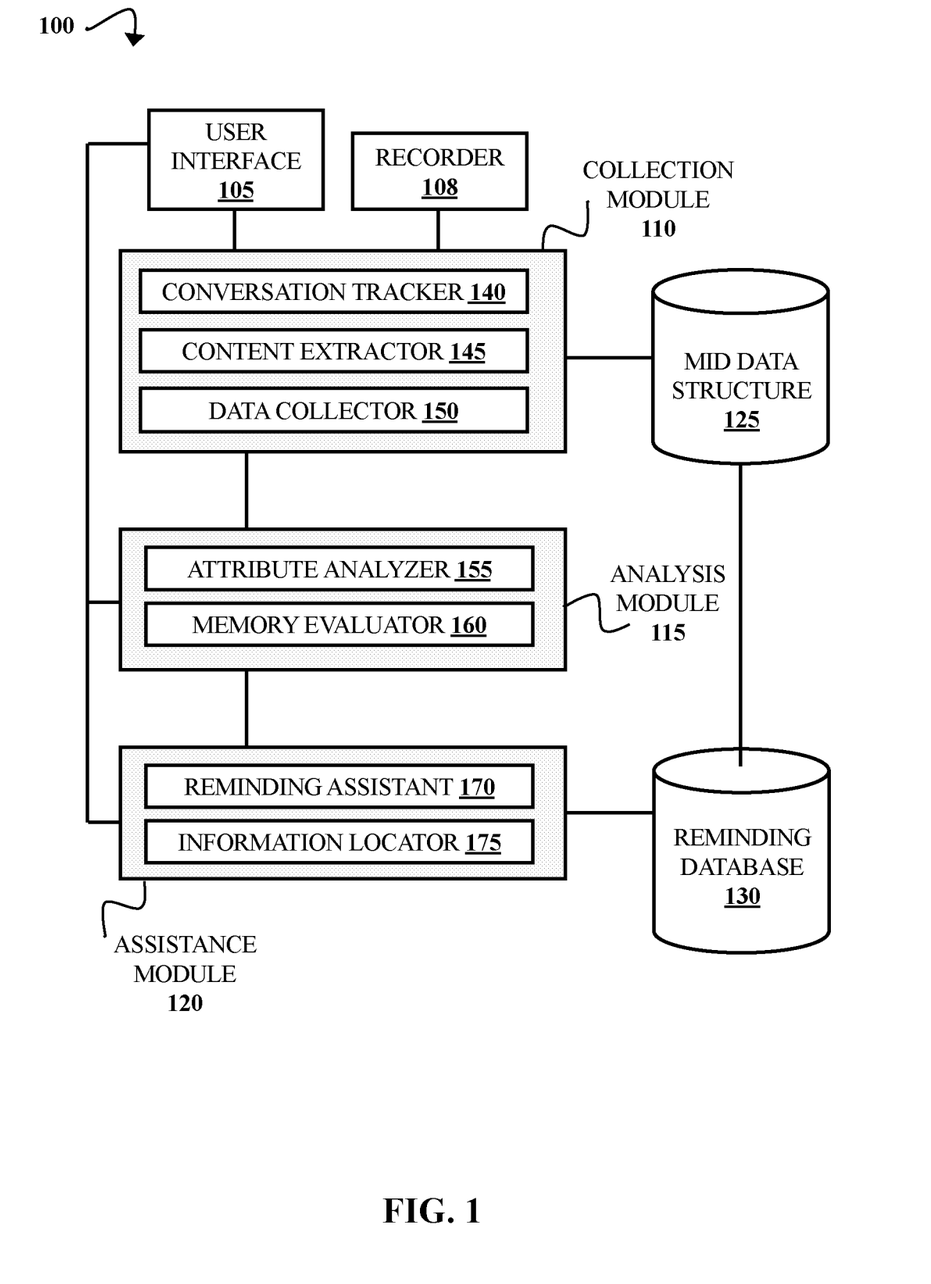
FIG. 1 is a block diagram illustrating a memory impairment detection and assistance environment, according to some embodiments of the present disclosure.

FIG. 1 is a block diagram illustrating a memory impairment detection and assistance (MIDA) environment 100, according to some embodiments of the present disclosure. The MIDA environment 100 includes a user interface 105, a recorder 108, a collection module 110, an analysis module 115, an assistance module 120, a memory impairment detection (MID) data structure 125, and a reminding database 130. The collection module 110 includes a conversation tracker 140, a content extractor 145, and a data collector 150. The analysis module 115 includes an attribute analyzer 155 and a memory evaluator 160. Further, the assistance module 120 includes an information locator 175 and a reminding assistant 170.

In some embodiments, all of the illustrated components of environment 100 are in a single device (e.g., a smartphone or desktop computer). However, environment 100 can include multiple devices. For example, the user interface 105, recorder 108, and collection module 110 can be in one device (e.g., a mobile computing device), while the analysis module 115, assistance module 120, MID data structure 125, and reminding database 130 can on at least one additional device (e.g., a desktop computer and/or remote server). Herein, anyone who interacts with the user interface 105 can be referred to as a "user". However, in order to aid explanation, a user whose memory is or is suspected of being impaired is referred to herein as a "designated user". Other users can include associates of the designated user (e.g., people who frequently interact with the individual, such as family, friends, caregivers, etc.) or any other entity interacting with the MIDA environment 100.

The user interface 105 is presented on a display device (e.g., a smartphone screen or the lenses of a wearable augmented reality device). The user interface 105 provides fields for entering information about the designated user, such as name, age, languages spoken, geography, medical history, daily routines, etc. The information about the designated user can optionally be stored in a profile for the designated user. The user interface 105 can also include fields for selecting settings, inputting assistance requests, and entering information about the user's associates (e.g., their respective names and relationships to the designated user). Settings and assistance requests are discussed in greater detail below. In some embodiments, the user interface 105 provides interactive activities for memory improvement and brain stimulation (e.g., puzzles, memory exercises, etc.).

The recorder 108 records audio data from conversations that include the designated user. However, in some embodiments, the recorder 108 can also record videos or still images. Any conventional recording device can be used. For example, the recorder 108 can be an audio recorder and, optionally, camera included in a mobile phone, a laptop or desktop computer, an augmented reality headset, or an external recording device in communication with a device that includes the collection module 110. The audio data can be collected from conversations conducted in person, as well as conversations conducted over the telephone or using a video and/or audio conference service. Audio data collected by the recorder 108 is transformed into data that a processor can process (e.g., digitally encoded).

The conversation tracker 140 receives, from the recorder 108, digitized audio data from spoken language (computer-readable speech data) through at least one channel. The channel or channels can be any type of transmission medium, such as a wire, cable, optical fiber, wireless signals, etc. The conversation tracker 140 can use at least one speech-to-text engine to decode the computer-readable speech data. The speech-to-text engine or engines use models (e.g., acoustic models, language models, phonetic word models, sentence models, etc.) to detect and recognize features of the speech data. An example of a modeling approach that can be used classify these language features is an artificial neural network, such as a convolutional neural network. However, any speech-to-text decoding method known in the art can be used (e.g., statistical modeling, Hidden Markov Models (HMM), lattice-based analysis, entropy-based speech segmentation algorithms, CMUSphinx, etc.). In some embodiments, the text can be supplemented or replaced by manually transcribed speech.

Decoded speech data from the conversation tracker 140 is received by the content extractor 145. The content extractor 145 extracts linguistic features (e.g., number of words spoken and the identities of the words) and audio features (e.g., length of time spent speaking, length of pauses between words, and voice prints of participants) from the speech data. The content extractor 145 identifies conversation participants based on voiceprints, voice history (e.g., from audio data saved from a previous conversation), and/or speech context analysis (e.g., speaker self-introduction, keywords, relationship description, event description, etc.). However, the content extractor 145 can gather information from sources other than the conversation data. Examples of these sources are discussed in greater detail with respect to FIG. 2.

The data collector 150 selects data relevant to memory impairment from the extracted content, and saves this data ("MID data") in the MID data structure 125. As MID data is collected in real time, the data collector 150 iteratively updates and merges the new MID data with the MID data structure 125. The MID data includes elements such as conversation participant lists (e.g., designated user (first speaker), second speaker, third speaker, etc.) and correlated basic speech elements such as conversation topic types, names of events and places, names of people, relationships between the designated user and the respective named people (e.g., "parent/child" or "nurse/patient"). Further, the MID data structure 125 can include timestamps, location coordinates, and acoustic features (e.g., pause-to-word ratio, total duration of speech, mean pause duration, long and short pause counts, phonation rate, etc.). The data collector 150 can also select MID data to add to the reminding database 130. This is discussed in greater detail below.

The MID data structure 125 also includes categories of keywords that are indicative of memory impairment. Examples can include keywords associated with requests for repetition (e.g., huh, pardon, what, hmm, mention, hear, say, said, missed, again, repeat, etc.) and requests for specific information (e.g., why, who, did, describe, detail, more, etc.). However, any appropriate category can be used, such as keywords indicative of corrections (e.g., ohhh, no, wrong, etc.), hypothesis formation (e.g., remember, suppose, find, etc.), and metalinguistic comments (e.g., know, forget, understand, ask, mention, etc.). Additional keyword categories can include filler words (e.g., uh, um, but, so, well, because, er, like, etc.) and interrogative pronouns (e.g., who, what, where, when, how, why, etc.). The MID data structure 125 can also correlate words in the conversation data with parts of speech (e.g., pronouns, prepositions, verbs, nouns, adjectives, articles, etc.), as well as phonological features (e.g., mispronunciations).

The keywords stored in the MID data structure 125 are extracted from the conversation data in real time. As new MID data is received, new keywords can be added to the MID data structure 125, making the data structure 125 more accurate with respect to the designated user. Any appropriate machine learning techniques can be used to add new keywords (e.g., k-nearest neighbor imputation, synthetic minority oversampling technique, multilinear logistic regression, mixture density network, Bayesian prediction, logistic regression, clustering algorithms, independent component analysis, Markov decision processes, etc.). Further, it should be noted that other sources of keywords for determining memory impairment can be used in addition to the conversation data (e.g., DementiaBank by TalkBank or Carolina Conversations Collection (CCC) by Medical University of South Carolina).

The data collector 150 sends the MID data to the analysis module 115 as it is received or upon request (e.g., a user input request or a preset scheduled request). The attribute analyzer 155 measures values for predefined features associated with memory impairment based on the MID data. These features are referred to herein as attributes or MID attributes. Examples of attributes can include frequency of object misplacement, number of missed appointments, difficulty in recognizing family and friends, difficulty in following directions, difficulty in completing a sentence or remaining on topic, confusion about time or location, confusion about people, difficulty in remembering names of common objects or well-known places, difficulty in remembering names of close associates, etc. Attributes can also be measures of word specificity, richness of vocabulary, syntactic complexity, word or phrase repetition, number of incomplete words, and number of filler words. Determining values for multiple MID attributes allows detailed quantitative information about the designated user's memory deterioration to be gained. In some embodiments, a user can select one or more specific MID attributes to be analyzed. However, all predefined attributes are analyzed in other embodiments.

In some embodiments, the attribute analyzer 155 measures attribute values by detecting a quantity of associated keywords (e.g., a number of keywords associated with object misplacement). However, a variety of techniques for measuring attributes can be employed. For example, a value for an attribute measuring richness of vocabulary can be determined using techniques such as type-token ratio, average word length, Brunet's index, or Honore's statistic. A value for an attribute measuring word specificity can be determined from hypernym relationships between synonym sets that form hierarchical trees (e.g., for nouns and verbs) or bipolar scales between pairs of extremes (e.g., for adjectives and adverbs). Additionally, syntactic complexity can be measured based on ratio of clauses to sentences, lengths of production units (e.g., clauses, sentences, and T-units), coordination (e.g., coordinate phrases per clause or T-unit), subordination (e.g., clauses per T-unit and dependent clauses per clause or T-unit), and particular structures, (e.g., verb phrases per T-unit or complex nominals per clause or T-unit).

Values for attributes measuring the length and difficulty of sentences, words, and/or phrases can also be determined. For example, the average sentence length spoken by each conversation participant identified by the content extractor 145 can be measured in terms of the number of words used. Word and sentence difficulty can be calculated based on the numbers of characters, words, and sentences.

In some embodiments, keywords are combined with one or more attribute values in order to determine values for additional attributes. For example, keywords correlated with following directions combined with high values for attributes such as low syntactic complexity, lack of richness of vocabulary, repetition, lack of word specificity, number of incomplete words, and/or number of filler words could result in a high value for an attribute measuring difficulty in following directions. Attributes can also be based on location and/or time. For example, a value for an attribute measuring a frequency of missed appointments could be determined by identifying appointments and their locations from calendar data and/or keywords. Then, by detecting the location of the designated user at the time of an appointment (e.g., by keywords and/or location coordinates) the attribute analyzer 155 can determine whether the designated user arrived at the appointment on time.

Based on the values of the MID attributes determined by the attribute analyzer 155, the memory evaluator 160 determines whether the memory of the designated user is impaired and, if memory impairment is found, the level and type of impairment. By carrying out multiple memory evaluations over a period of time, the memory evaluator 160 can track the symptoms of progressive memory impairment as it begins, increases, decreases, or stabilizes. In some embodiments, the frequency of evaluations can be increased or decreased based on user input requests or automatically. For example, if no change is detected for several months, the frequency may be automatically reduced. However, the evaluation frequency can be preset as well.

The memory evaluator 160 evaluates memory impairment using one or more thresholds. One example of an evaluation threshold is a minimum number of MID attributes having values that cross (e.g., meet or surpass) a threshold MID attribute value. Threshold MID attribute values include maximum MID attribute values (e.g., maximum number of names forgotten) and/or minimum MID attribute values (e.g., minimum syntactic complexity). For example, an evaluation threshold could define memory impairment as being when at least 50% of MID attributes in a set of attributes have values that cross a threshold MID attribute value (e.g., values above a maximum MID attribute value and/or below a minimum MID attribute value). In some embodiments, MID attributes can be given different weights when calculating percentages of attributes in a set. Additionally, an evaluation threshold can be one or more particular combinations of MID attributes having values that cross threshold MID attribute values. In some embodiments, there is more than one evaluation threshold, each threshold indicating a different level of memory impairment. For example, impairment can be measured on a numeric scale (e.g., 0-10) or classified as being in different tiers (e.g., low, moderate, and severe).

The assistance module 120 provides memory assistance when a request to do so is received. The assistance module 120 includes a reminding assistant 170 that generates reminders based, at least in part, on MID data gathered in real time and evaluations of the designated user's memory. The designated user or another user can enter a request for assistance via the user interface 105. The request can also be automatically sent to the assistance module 120 based on a memory evaluation. For example, memory assistance can be automatically requested when the memory evaluator 160 determines memory impairment to be moderate or severe. Additionally, a user can optionally direct the assistance module 120 to cease providing memory assistance. In some embodiments, the user can program the reminding assistant 170 to provide assistance at scheduled times (e.g., only in the evening), specific memory impairment levels (e.g., severe), and/or in designated places (e.g., only at work).

The type and level of assistance provided by the assistance module 120 can also be automatically varied based on memory evaluation data from the memory evaluator 160. For example, when a memory impairment level is moderate, the reminding assistant 170 can provide pop-up messages on the user interface 105 offering to provide assistance (e.g., information searches, word suggestions, recommended activities, etc.). Then, the reminding assistant 170 can switch to automatic assistance if a subsequent memory evaluation indicates that the memory impairment level is severe. The type of assistance can vary based on which MID attributes are most significant to the designated user (e.g., most impaired or most frequently needed).

The reminding assistant 170 determines how and when to provide specific assistance based on memory impairment signals. For example, a memory impairment signal may indicate that the designated user does not recognize the name Martha when the name is mentioned in a tracked conversation. This memory impairment signal may include keywords such as "who", "forgot", and "Martha". In some embodiments, all names detected in real time are treated as memory impairment signals if the designated user has memory impairment related to an attribute measuring difficulty in name recognition. The reminding assistant 170 can then send a request to the information locator 175 to identify Martha. The information locator 175 obtains this information from the reminding database 130.

The reminding database 130 contains information from the MID data structure 125 that can be provided to the designated user by the reminding assistant 170. This information is related to the predefined attributes, and is selected by the data collector 150. Because only selected information is stored in the reminding database 130, the information locator 175 is not required to search the entire MID database 125 when a memory impairment signal is received. In some embodiments, the data collector 150 adds all data from a preset list of categories to the reminding database 130 (e.g., names and descriptions of associates, location coordinates and associated keywords, dates and times of appointments, etc.). However, information stored in the reminding database 130 can also be selected by a user and/or automatically selected based on a memory evaluation. In a simplified example, if the attribute analyzer 155 and memory evaluator 160 determine that a designated user has moderate memory impairment related only to the attribute of remembering names, the data collector 150 can exclusively add names of people, as well as contextual information correlated with the names, to the reminding database 130.

The reminding database 130 can be updated as the MID data structure 125 receives new MID data. For example, if a designated user or another conversation participant says, "I'm leaving the umbrella on the porch," the MID data structure 125 can be updated to include a correlation between the object "umbrella" and the location "porch". This information can also be added to the reminding database 130. Later, if a memory impairment signal indicates that the designated user cannot find the umbrella (e.g., based on keywords such as "where", "leave", and "umbrella"), the reminding assistant 170 will automatically notify the designated user that the umbrella may be on the porch. In another example, the designated user can ask another conversation participant where a particular object is located. If the conversation participant answers the question, the location information can be automatically added to the MID data structure 125 and reminding database 130.

The information obtained from the reminding database 130 by the information locator 175 is provided to the designated user by the reminding assistant 170. For example, a reminder in response to a forgotten name could include a pop-up message or audio message supplying at least one suggested name. This reminder could also include more detailed information than a suggested name (e.g., a description of the person, a graphical image, a link to a social networking profile, etc.). In some embodiments, the designated user can request additional information upon receiving an initial name suggestion. For example, the user interface 105 may display a pop-up message with the text "Martha Identified". The designated user could (e.g., by speaking a command or selecting an option on the user interface) click on the message to view more information or dismiss the message. Further, the designated user could optionally confirm the information or indicate that some or all of the provided information is incorrect. The reminding database 130 and MID data structure 125 can then be updated to reflect this.

Figure 2:
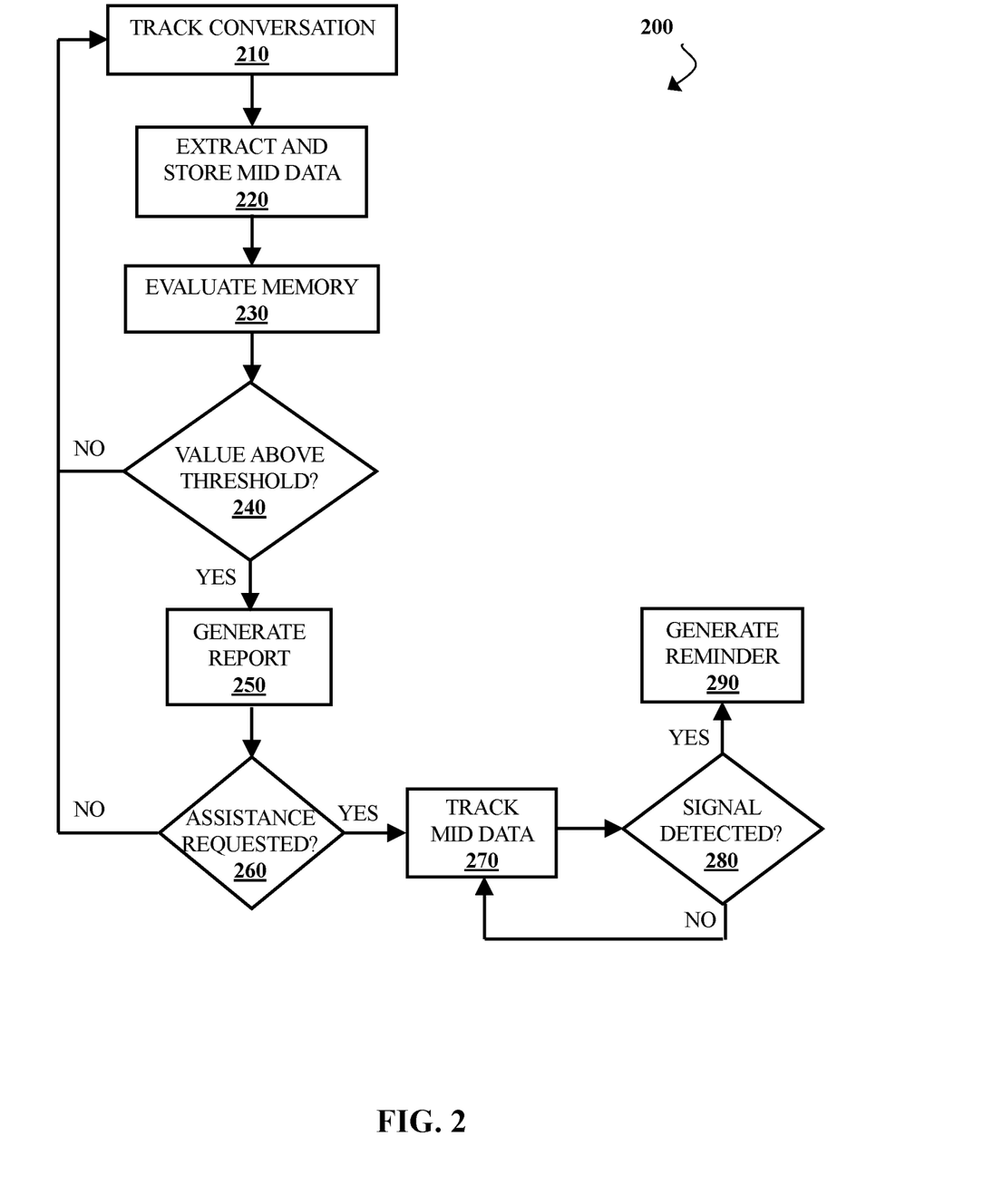
FIG. 2 is a flow diagram illustrating a process of detecting memory impairment and providing reminding assistance, according to some embodiments of the present disclosure.

FIG. 2 is a flow diagram illustrating a process of memory impairment detection and assistance. To illustrate process 200, but not to limit embodiments, FIG. 2 is described within the context of the MIDA environment 100 of FIG. 1. Where elements described with respect to FIG. 2 are identical to elements shown in FIG. 1, the same reference numbers are used in both figures.

Process 200 includes gathering conversation data. This is illustrated at step 210. Audio conversation data collected by the recorder 108 is converted to computer-readable speech data by the conversation tracker 140. In addition to the audio data, conversation data can be gathered from text data (e.g., email, social networking application posts, text messaging services, etc.) by the conversation tracker 140. In some embodiments, conversations are continuously tracked. However, the tracking may be turned on or off by a user or automatically at scheduled times. Additionally, conversation tracking can be location-based. For example, conversations can optionally be tracked only when a device that includes the recorder 108 (e.g., a smartphone) is detected in a particular location (e.g., using Bluetooth beacons, Wi-Fi triangulation, or geolocation). The conversation tracking time settings can also be adjusted automatically based on memory evaluations.

Memory impairment detection (MID) data is then extracted and stored. This is illustrated at step 220. Information including speaker identities, linguistic features, and audio features is extracted from the conversation data by the content extractor 145. The content extractor 145 can also gather information such as timestamps and location coordinates of a digital computing device belonging to the designated user (e.g., by geolocation, Bluetooth beacons, Wi-Fi triangulation, etc.). The elements extracted by the content extractor 145 can be supplemented by user-input information in some embodiments. Additionally, if the recorder 108 includes a camera, information about speaker identities and the designated user's environment could be obtained from video data using techniques commonly known in the art (e.g., facial recognition algorithms).

The data collector 150 selects MID data from the extracted information, and adds this data to the MID data structure 125. The MID data structure 125 is discussed in greater detail with respect to FIG. 1. Additionally, the data collector 150 selects MID data related to at least one MID attribute and adds this data to the reminding database 130. The MID data can be selected based on preset attributes or it can be adjusted based on attribute analysis in subsequent steps. This is discussed in greater detail below.

Based on the gathered MID data, a memory evaluation is conducted for the designated user. This is illustrated at step 230. The data collector 150 sends the MID data to the analysis module 115, and the attribute analyzer 155 uses the MID data to determine values for at least one predefined attribute (e.g., frequency of object misplacement, number of missed appointments, difficulty in recognizing family and friends, difficulty in following directions, difficulty in completing a sentence or remaining on topic, confusion about time or location, confusion about people, difficulty in remembering names of common objects or well-known places, difficulty in remembering names of close associates, etc.). Additional attributes and techniques for determining attribute values are discussed in greater detail with respect to FIG. 1.

Based on the attribute values, the memory evaluator 160 carries out the memory evaluation. The memory evaluator 160 determines whether the memory of the designated user is impaired. In some embodiments, the memory evaluator 160 also determines if the memory impairment is at a particular level (e.g., low, moderate, or severe) or of a particular type (e.g., primarily occurring in the evening or primarily affecting word finding ability). In some embodiments, the memory evaluator 160 evaluates memory impairment at regular intervals (e.g., daily, weekly, monthly, etc.). However, evaluations can also be carried out as MID attributes are updated and/or when directed by a user input command. Regular memory evaluations allow the symptoms of memory impairment to be tracked over time.

The memory evaluator 160 determines whether the memory impairment level is above an evaluation threshold. This is illustrated at step 240. For example, there can be three evaluation thresholds, each threshold corresponding to a memory impairment level (e.g., low, moderate, and high). Each threshold can be a percentage of MID attribute values from the set of MID attributes analyzed by the attribute analyzer 155 that cross a threshold attribute value. The respective thresholds for the levels low, moderate, and high may be 25%, 50%, and 75% of the MID attributes having values that meet or surpass threshold attribute values (e.g., values above maximum and/or below minimum attribute values). However, any appropriate threshold can be used to evaluate memory. For example, the evaluation thresholds can be specific attributes or specific numbers of attributes having values crossing threshold attribute values. If the memory impairment level is not above any evaluation threshold, process 200 returns to step 210.

However, if the memory impairment level is above at least one evaluation threshold, a report indicating that memory impairment has been detected is generated. This is illustrated at step 250. The report provides a description of the memory evaluation. The report can contain any level of detail. For example, the report may simply indicate the level of impairment (e.g., "high"). However, the report can also provide information such as analyses of individual attributes, comparison to earlier evaluations, predictions about future symptoms, and suggested actions (e.g., increase frequency of memory evaluation, input additional information, engage in recommended exercises or other activities, speak to a medical professional, etc.). In some embodiments, the level of detail in the report can be adjusted based on user-input settings.

The report can be displayed on the user interface 105 and/or provided as an audio message. In some embodiments, the report is accessed by selecting an option on the user interface 105 or speaking an audio command. However, the report can also be provided automatically. In some instances, the report includes a notification (e.g., a pop-up message, an email, an audio message or alarm, etc.). It should also be noted that, in addition to returning to step 210, process 200 can include generating a report when memory impairment is not detected (e.g., upon user request). For example, a requested report can indicate that no memory impairment was found and, optionally, include attribute analyses.

It is then determined whether there is a request for assistance. This is illustrated at step 260. In some embodiments, a request for assistance is automatically generated based on the memory evaluation or on a schedule (e.g., daily at 7 PM). However, the request can also be input by a user. Additionally, the user may be prompted to accept or dismiss assistance in a pop-up message or other notification offering assistance. If there is no request for assistance, or if an automatic assistance request has been dismissed by the user, process 200 returns to step 210, and continues to track the conversation.

However, if there is a request for assistance, the assistance module 120 begins to track MID data as it is received in real time. This is illustrated at step 270. Based on the contents of the MID data, the reminding assistant 170 determines when to provide assistance. Additionally, the reminding assistant 170 uses the MID data and MID attribute values to determine what type of assistance is appropriate. The data collector 150 continues to send MID data to the assistance module 120 as the data is received until the collection module 110, analysis module 115, and/or assistance module 120 are instructed to stop (e.g., according to user input instructions, a schedule, or a new memory evaluation result).

The reminding assistant 170 detects whether there is a memory impairment signal in the received MID data. This is illustrated at step 280. A memory impairment signal includes received MID data correlated with elements in the MID data structure 125 that indicate a need for and/or type of assistance. In some instances, memory impairment signals include keywords, such as keywords correlated with an inability to remember a name, as well as contextual information related to the forgotten name. For example, if the designated user asks, "Who did I meet at the event yesterday?", the memory impairment signal could include the keywords "who", "event", and "yesterday". However, memory impairment signals can include a variety of MID data, such as timestamps and location coordinates. If no memory impairment signal is detected, process 200 returns to tracking MID data at step 270.

However, if a memory impairment signal is detected, a reminder is generated. This is illustrated at step 290. Based on the memory impairment signal received by the reminding assistant 170, the information locator 175 obtains information from the reminding database 130. For example, when a memory impairment signal indicating that a name has been forgotten is received, the information locator 175 can locate the forgotten name in the reminding database 130 based on contextual information related to the name. The contextual information can include the time of day, location, voiceprint, keywords (e.g., "event" and "yesterday"), etc. A name reminder is then generated and presented to the designated user by the reminding assistant 170 (e.g., on the user interface 105 or in an audio message).

In another example, a memory impairment signal can be a time. If the designated user has difficulty remembering appointments (e.g., as indicated by previously determined MID attribute values or user input settings) a memory impairment signal could be received ten minutes before every hour from 7 AM to 6 PM. Then, if the information locator 175 finds an appointment scheduled at 8 AM in the reminding database 130 upon receiving the 7:50 AM signal, a reminder notifying the designated user of the appointment at 8 AM can be generated. Additionally, a memory impairment signal can be a location coordinate. For example, a reminder containing a grocery list can be generated when the designated user enters a grocery store. Upon generating the reminder, process 200 can return to operation 210 or it can end if instructed to do so (e.g., by a user input instruction or automatically based on preset instructions).

Figure 3:
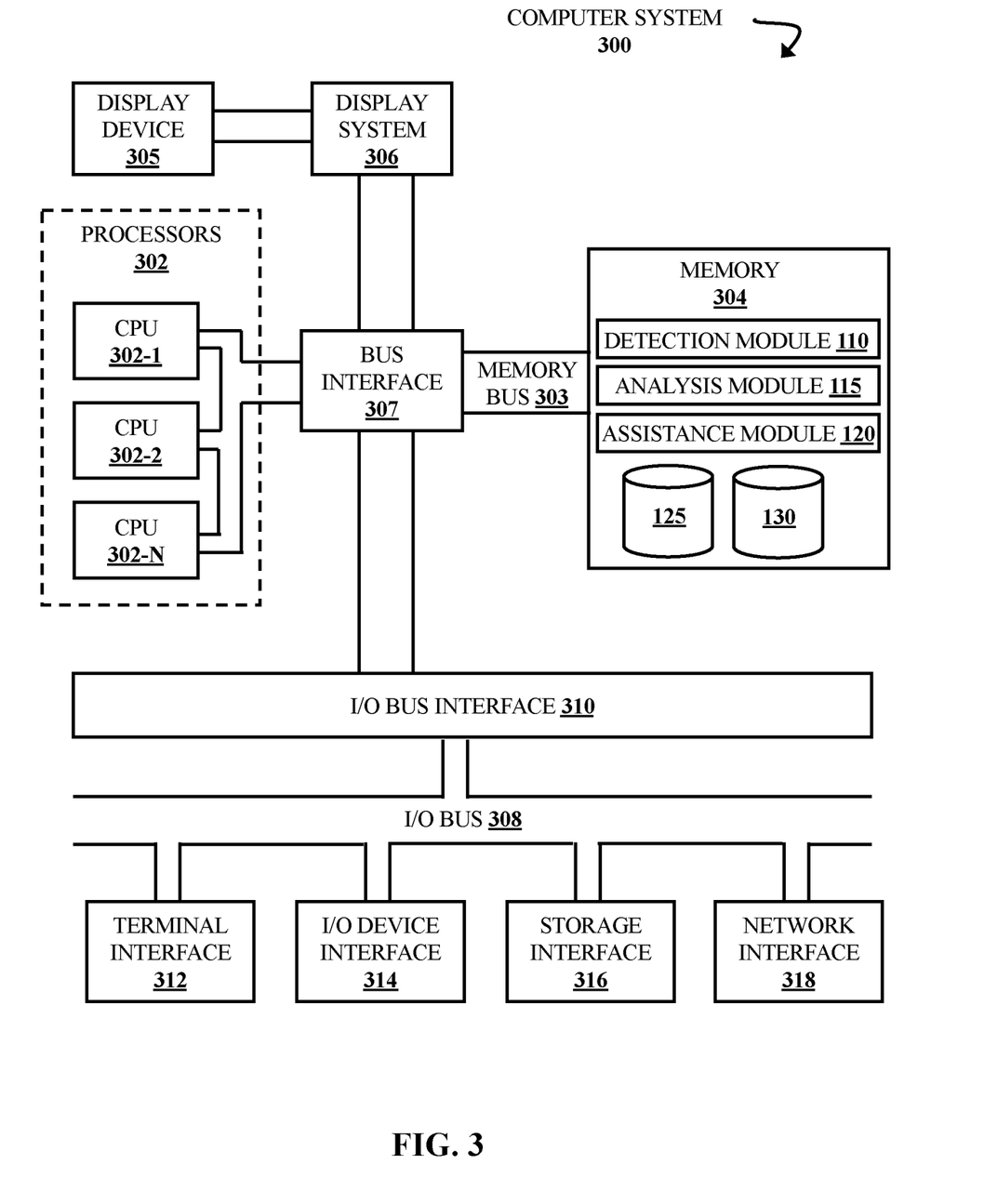
FIG. 3 is a block diagram illustrating a computer system, according to some embodiments of the present disclosure.

FIG. 3 is a high-level block diagram illustrating an exemplary computer system 300 that can be used in implementing one or more of the methods, tools, components, and any related functions described herein (e.g., using one or more processor circuits or computer processors of the computer). In some embodiments, the major components of the computer system 300 comprise one or more processors 302, a memory subsystem 304, a terminal interface 312, a storage interface 316, an input/output device interface 314, and a network interface 318, all of which can be communicatively coupled, directly or indirectly, for inter-component communication via a memory bus 303, an input/output bus 308, bus interface unit 307, and an input/output bus interface unit 310.

The computer system 300 contains one or more general-purpose programmable central processing units (CPUs) 302-1, 302-2, and 302-N. Herein, these processors are collectively referred to as the CPU 302. In some embodiments, the computer system 300 contains multiple processors typical of a relatively large system; however, in other embodiments the computer system 300 can alternatively be a single CPU system. Each CPU 302 may execute instructions stored in the memory subsystem 304 and can include one or more levels of on-board cache.

The memory 304 can include a random-access semiconductor memory, storage device, or storage medium (either volatile or non-volatile) for storing or encoding data and programs. In some embodiments, the memory 304 represents the entire virtual memory of the computer system 300, and may also include the virtual memory of other computer systems coupled to the computer system 300 or connected via a network. The memory 304 is conceptually a single monolithic entity, but in other embodiments the memory 304 is a more complex arrangement, such as a hierarchy of caches and other memory devices. For example, memory may exist in multiple levels of caches, and these caches may be further divided by function, so that one cache holds instructions while another holds non-instruction data, which is used by the processor or processors. Memory can be further distributed and associated with different CPUs or sets of CPUs, as is known in any of various so-called non-uniform memory access (NUMA) computer architectures. The memory 304 also contains a detection module 110, an analysis module 115, an assistance module 120, a memory impairment detection (MID) data structure 125, and a reminding database 130.

These components are illustrated as being included within the memory 304 in the computer system 300. However, in other embodiments, some or all of these components may be on different computer systems and may be accessed remotely, e.g., via a network. The computer system 300 may use virtual addressing mechanisms that allow the programs of the computer system 300 to behave as if they only have access to a large, single storage entity instead of access to multiple, smaller storage entities. Thus, though the detection module 110, analysis module 115, assistance module 120, memory impairment detection (MID) data structure 125, and reminding database 130 are illustrated as being included within the memory 304, components of the memory 304 are not necessarily all completely contained in the same storage device at the same time. Further, although these components are illustrated as being separate entities, in other embodiments some of these components, portions of some of these components, or all of these components may be packaged together.

In some embodiments, the detection module 110, analysis module 115, and assistance module 120 include instructions that execute on the processor 302 or instructions that are interpreted by instructions that execute on the processor 302 to carry out the functions as further described in this disclosure. In other embodiments, the detection module 110, analysis module 115, and assistance module 120 are implemented in hardware via semiconductor devices, chips, logical gates, circuits, circuit cards, and/or other physical hardware devices in lieu of, or in addition to, a processor-based system. In other embodiments, the detection module 110, analysis module 115, and assistance module 120 include data in addition to instructions.

Although the memory bus 303 is shown in FIG. 3 as a single bus structure providing a direct communication path among the CPUs 302, the memory subsystem 304, the display system 306, the bus interface 307, and the input/output bus interface 310, the memory bus 303 can, in some embodiments, include multiple different buses or communication paths, which may be arranged in any of various forms, such as point-to-point links in hierarchical, star or web configurations, multiple hierarchical buses, parallel and redundant paths, or any other appropriate type of configuration. Furthermore, while the input/output bus interface 310 and the input/output bus 308 are shown as single respective units, the computer system 300 may, in some embodiments, contain multiple input/output bus interface units 310, multiple input/output buses 308, or both. Further, while multiple input/output interface units are shown, which separate the input/output bus 308 from various communications paths running to the various input/output devices, in other embodiments some or all of the input/output devices may be connected directly to one or more system input/output buses.

The computer system 300 may include a bus interface unit 307 to handle communications among the processor 302, the memory 304, a display system 306, and the input/output bus interface unit 310. The input/output bus interface unit 310 may be coupled with the input/output bus 308 for transferring data to and from the various input/output units. The input/output bus interface unit 310 communicates with multiple input/output interface units 312, 314, 316, and 318, which are also known as input/output processors (IOPs) or input/output adapters (IOAs), through the input/output bus 308. The display system can include the user interface 105 (illustrated in FIG. 1). Further, the display system 306 may include a display controller. The display controller may provide visual, audio, or both types of data to a display device 305. The display system 306 may be coupled with a display device 305, such as a standalone display screen, computer monitor, television, or a tablet or handheld device display. In alternate embodiments, one or more of the functions provided by the display system 306 may be on board a processor 302 integrated circuit. In addition, one or more of the functions provided by the bus interface unit 307 may be on board a processor 302 integrated circuit.

In some embodiments, the computer system 300 is a multi-user mainframe computer system, a single-user system, or a server computer or similar device that has little or no direct user interface, but receives requests from other computer systems (clients). Further, in some embodiments, the computer system 300 is implemented as a desktop computer, portable computer, laptop or notebook computer, tablet computer, pocket computer, telephone, smart phone, network switches or routers, or any other appropriate type of electronic device.

It is noted that FIG. 3 is intended to depict the representative major components of an exemplary computer system 300. In some embodiments, however, individual components may have greater or lesser complexity than as represented in FIG. 3, Components other than or in addition to those shown in FIG. 3 may be present, and the number, type, and configuration of such components may vary.

In some embodiments, the data storage and retrieval processes described herein could be implemented in a cloud computing environment, which is described below with respect to FIGS. 4 and 5. It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
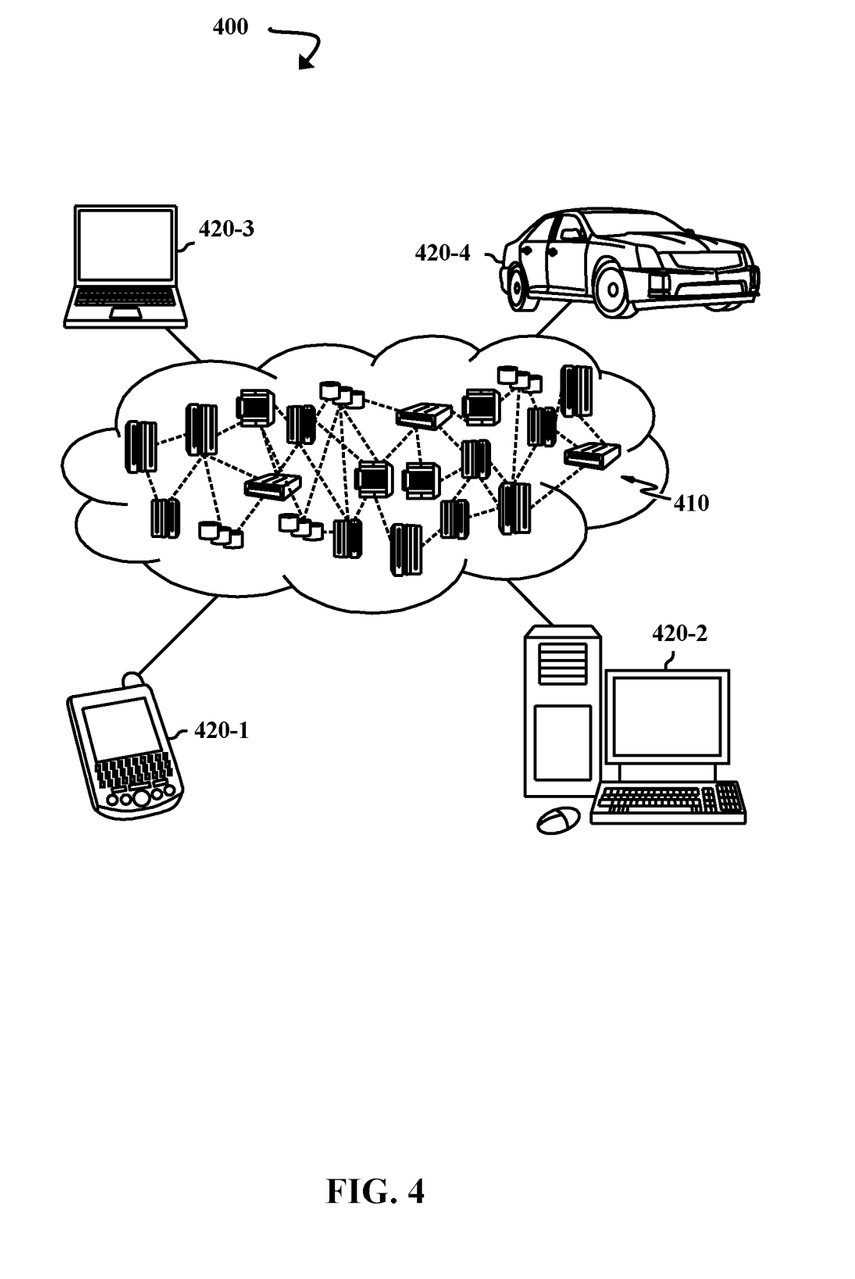
FIG. 4 is a block diagram illustrating a cloud computing environment, according to some embodiments of the present disclosure.

FIG. 4 is a block diagram illustrating a cloud computing environment 400, according to some embodiments of the present disclosure. As shown, cloud computing environment 400 includes one or more cloud computing nodes 410 with which local computing devices used by cloud consumers such as, for example, personal digital assistant (PDA) or cellular telephone 420-1, desktop computer 420-2, laptop computer 420-3, and/or automobile computer system 420-4 may communicate. Nodes 410 may communicate with one another. They may be grouped (not shown) physically or virtually, in one or more networks, such as Private, Community, Public, or Hybrid clouds as described hereinabove, or a combination thereof. This allows cloud computing environment 400 to offer infrastructure, platforms, and/or software as services for which a cloud consumer does not need to maintain resources on a local computing device. It is understood that the types of computing devices 420-1-420-4 shown in FIG. 4 are intended to be illustrative only and that computing nodes 410 and cloud computing environment 400 can communicate with any type of computerized device over any type of network and/or network addressable connection (e.g., using a web browser).

Figure 5:
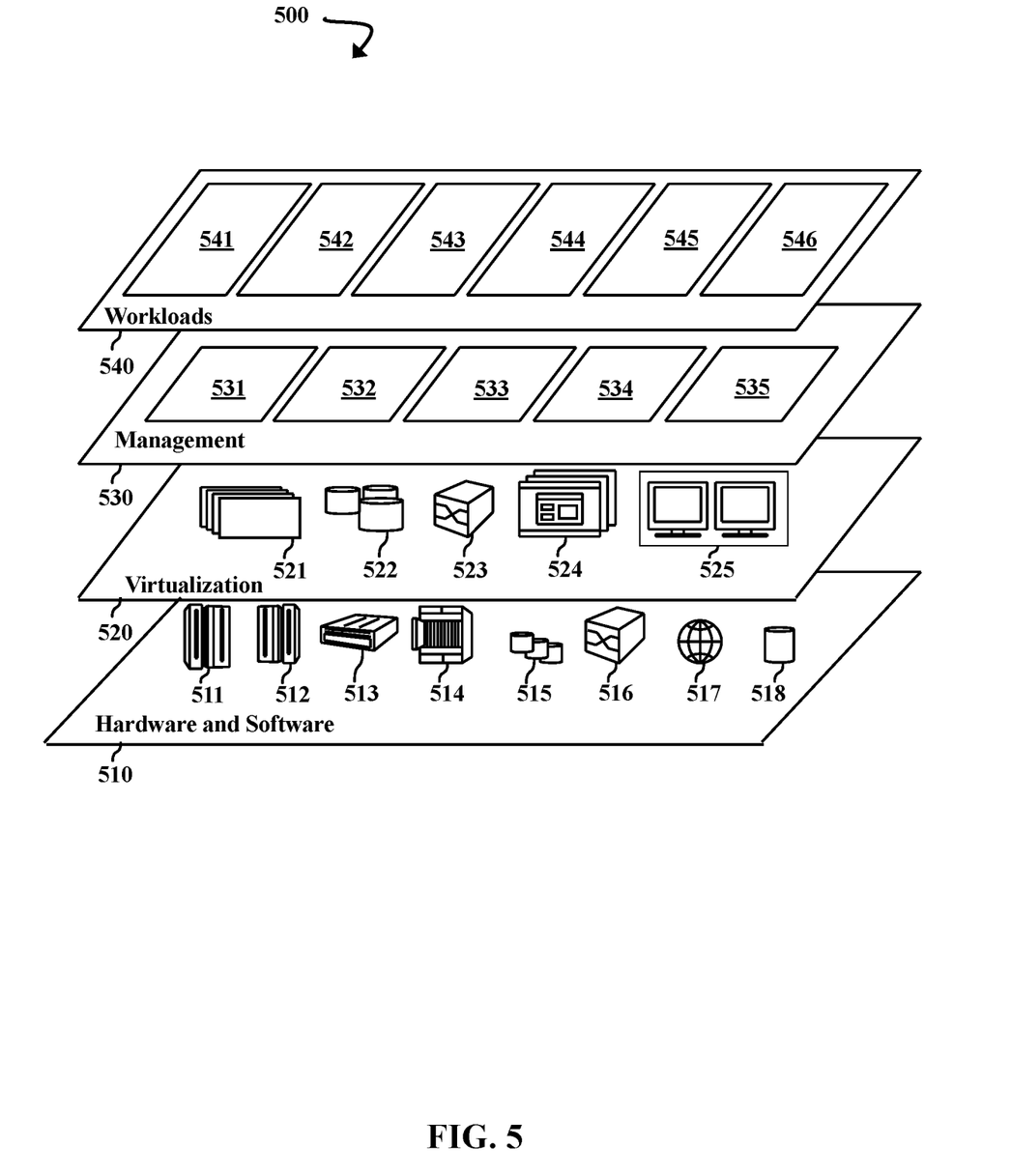
FIG. 5 is a block diagram illustrating a set of functional abstraction model layers provided by the cloud computing environment, according to some embodiments of the present disclosure.

FIG. 5 is a block diagram illustrating a set of functional abstraction model layers 500 provided by the cloud computing environment 400, according to some embodiments of the present disclosure. It should be understood in advance that the components, layers, and functions shown in FIG. 5 are intended to be illustrative only and embodiments of the invention are not limited thereto. As depicted, the following layers and corresponding functions are provided:

Hardware and software layer 510 includes hardware and software components. Examples of hardware components include: mainframes 511; RISC (Reduced Instruction Set Computer) architecture-based servers 512; servers 513; blade servers 514; storage devices 515; and networks and networking components 516. In some embodiments, software components include network application server software 517 and database software 518.

Virtualization layer 520 provides an abstraction layer from which the following examples of virtual entities may be provided: virtual servers 521; virtual storage 522; virtual networks 523, including virtual private networks; virtual applications and operating systems 524; and virtual clients 525.

In one example, management layer 530 provides the functions described below. Resource provisioning 531 provides dynamic procurement of computing resources and other resources that are utilized to perform tasks within the cloud computing environment. Metering and Pricing 532 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 533 provides access to the cloud computing environment for consumers and system administrators. Service level management 534 provides cloud computing resource allocation and management such that required service levels are met. Service Level Agreement (SLA) planning and fulfillment 535 provide pre-arrangement for, and procurement of, cloud computing resources for which a future requirement is anticipated in accordance with an SLA.

Workloads layer 540 provides examples of functionality for which the cloud computing environment can be utilized. Examples of workloads and functions that can be provided from this layer include: mapping and navigation 541; software development and lifecycle management 542; virtual classroom education delivery 543; data analytics processing 544; transaction processing 545; and detecting and assisting with memory impairment 546.

The present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out steps of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and step of possible implementations of systems, methods, and computer program products according to various embodiments of the present disclosure. In this regard, each block in the flowchart or block diagrams may represent a component, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Although the present disclosure has been described in terms of specific embodiments, it is anticipated that alterations and modification thereof will become apparent to the skilled in the art. Therefore, it is intended that the following claims be interpreted as covering all such alterations and modifications as fall within the true spirit and scope of the disclosure.

What is claimed is:

1. A method for providing reminding assistance, comprising:
   determining, based on memory impairment detection (MID) data, values for one or more attributes;
   determining that at least one attribute from the one or more attributes has a value that crosses a threshold attribute value;
   selecting, from a MID data structure, MID data related to the at least one attribute;
   adding the selected MID data to a reminding database;
   receiving a memory impairment signal; and
   generating, in response to receiving the memory impairment signal, a reminder that includes information selected from the reminding database.

2. The method of claim 1, further comprising: determining, based on the values for the one or more attributes, a level of memory impairment for a designated user.

3. The method of claim 1, further comprising:
   recording conversation data;
   extracting MID data from the conversation data in real time; and
   updating the MID data structure with the extracted MID data.

4. The method of claim 3, wherein the MID data includes the memory impairment signal.

5. The method of claim 3, further comprising:
   selecting MID data from the extracted MID data related to the at least one attribute; and
   updating the reminding database with the selected MID data from the extracted MID data.

6. The method of claim 1, wherein the one or more attributes are selected from a group consisting of frequency of object misplacement, number of missed appointments, difficulty in recognizing family and friends, difficulty in following directions, difficulty in completing a sentence or remaining on topic, confusion about time or location, confusion about people, difficulty in remembering names of common objects or well-known places, and difficulty in remembering names of close associates.

7. The method of claim 1, wherein the one or more attributes are selected from a group consisting of word specificity, richness of vocabulary, syntactic complexity, word or phrase repetition, number of incomplete words, and number of filler words.

8. The method of claim 1, wherein the reminder is displayed on a user interface.

\* \* \* \* \*